(12) United States Patent
Grossmann et al.

(10) Patent No.: US 7,010,900 B2
(45) Date of Patent: Mar. 14, 2006

(54) BEVERAGE BOTTLING PLANT FOR FILLING BOTTLES WITH A LIQUID BEVERAGE FILLING MATERIAL, AND A CLEANING DEVICE FOR CLEANING BOTTLES IN A BEVERAGE BOTTLING PLANT

(75) Inventors: Holger Grossmann, Hamburg (DE); Thomas Herold, Duvensee (DE)

(73) Assignee: KHS Maschinen- Und Anlagenbau AG, Dortmund (DE)

( * ) Notice: Subject to any disclaimer, the term of this patent is extended or adjusted under 35 U.S.C. 154(b) by 0 days.

(21) Appl. No.: 10/801,924

(22) Filed: Mar. 16, 2004

(65) Prior Publication Data
US 2004/0237466 A1 Dec. 2, 2004

Related U.S. Application Data

(63) Continuation-in-part of application No. PCT/EP02/08860, filed on Aug. 8, 2002.

(30) Foreign Application Priority Data
Sep. 17, 2001 (DE) ................. 101 45 818

(51) Int. Cl.
  *B65B 55/00* (2006.01)
(52) U.S. Cl. .................. 53/167; 53/266.1; 53/272; 134/169 R; 422/28; 422/292; 422/302

(58) Field of Classification Search ............... 422/1, 422/28, 292, 302; 134/74, 122 R, 166 R, 134/169 R, 100.1, 102.1, 102.2; 53/167, 53/431, 432, 425, 426, 266.1, 267, 272, 275
See application file for complete search history.

(56) References Cited

U.S. PATENT DOCUMENTS

| 4,537,749 | A | * | 8/1985 | Hick ..................... 422/304 |
| 4,631,173 | A | * | 12/1986 | Muller et al. ............ 422/28 |
| 5,178,841 | A | * | 1/1993 | Vokins et al. ........... 422/298 |
| 5,713,403 | A | * | 2/1998 | Clusserath et al. ....... 141/101 |
| 5,997,827 | A | * | 12/1999 | Mezger et al. ........... 422/292 |
| 6,622,457 | B1 | * | 9/2003 | Kurth .................... 53/425 |
| 6,786,249 | B1 | * | 9/2004 | Armbruster et al. ...... 141/92 |
| 2002/0159915 | A1 | * | 10/2002 | Zelina et al. ............ 422/3 |

\* cited by examiner

*Primary Examiner*—Stephen F. Gerrity
*Assistant Examiner*—Thanh Truong
(74) *Attorney, Agent, or Firm*—Nils H. Ljungman & Associates

(57) ABSTRACT

There is now provided a beverage bottling plant for filling bottles with a liquid beverage filling material in a beverage bottling plant, and a cleaning device with a pair of nozzles transversely disposed with respect to one another for introduction of cleaning medium into a stream of air and for introduction a stream of air into a cleaning medium.

20 Claims, 3 Drawing Sheets

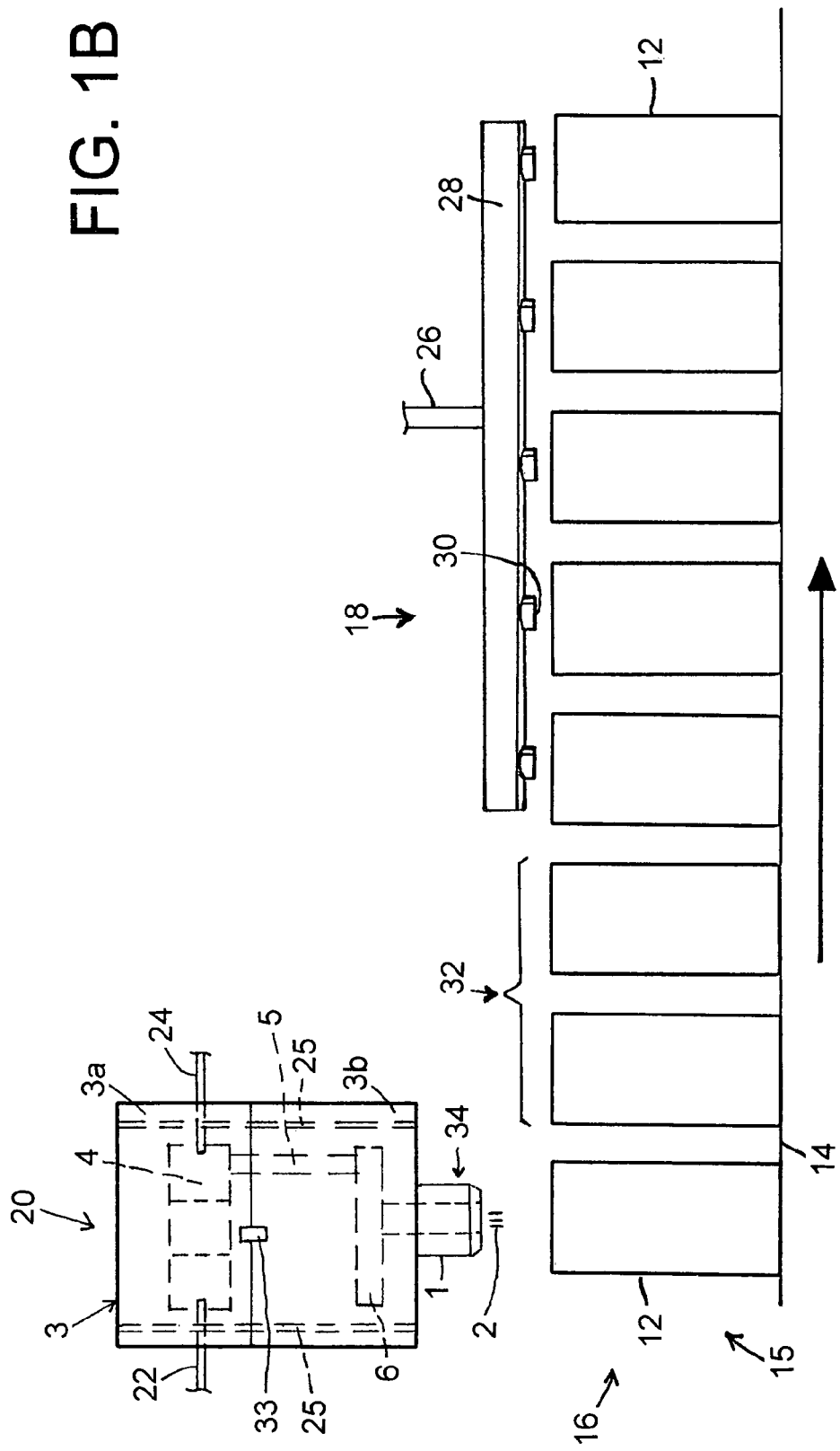

US 7,010,900 B2

BEVERAGE BOTTLING PLANT FOR FILLING BOTTLES WITH A LIQUID BEVERAGE FILLING MATERIAL, AND A CLEANING DEVICE FOR CLEANING BOTTLES IN A BEVERAGE BOTTLING PLANT

CONTINUING APPLICATION DATA

This application is a Continuation-In-Part application of International Patent Application No. PCT/EP02/08860, filed on Aug. 8, 2002, which claims priority from Federal Republic of Germany Patent Application No. 101 45 818.5, filed on Sep. 17, 2001. International Patent Application No. PCT/EP02/08860 was pending as of the filing date of this application. The United States was an elected state in International Patent Application No. PCT/EP02/08860.

BACKGROUND

1. Technical Field

The application relates to a beverage bottling plant for filling bottles with a liquid beverage filling material, and a cleaning device for cleaning bottles in a beverage bottling plant.

2. Background Information

Beverage bottling plants for filling bottles with liquid beverage filling material have a filling machine for filling bottles, cans with a liquid in a container filling process. Such a filling machine usually comprises a plurality of filling positions, with each filling position having a filling element to fill a corresponding bottle with liquid beverage filling material. There is possibly also provided an apparatus to move empty bottles to a filling element, and each filling element being configured and disposed to receive corresponding bottles to be filled from said apparatus to move empty bottles. Upon filling, an apparatus removes a filled bottle from a filling element. There may possibly also be provided an apparatus to hold a bottle to be filled in sealing attitude at a filling element, and each filling element having a portion to introduce at least one process pressure into the interior space of a corresponding bottle, as well as at least one pressure sensor for each filling element, each sensor being disposed and configured to sense a pressure related to the interior of a corresponding bottle that is connected with the corresponding filling element, and each sensor being configured to produce at least one indication representative of a sensed pressure related to the interior of a corresponding bottle. There may also be provided a controller that is configured to receive from a corresponding sensor at least one indication representative of a sensed pressure related to the interior of a bottles; and apparatus configured to control at least one process parameter related to filling a bottle in the filling machine. That controller may be further configured to control the control apparatus for the at least one process parameter of the filling machine.

Also known are filling plant systems that include a cleaning station to rinse or otherwise clean containers such as bottles and the like.

Thus, a beverage bottling plant for filling bottles with a liquid beverage filling material can possibly comprise a cleaning station to clean bottles, a beverage filling machine with a plurality of beverage filling positions, each beverage filling position having a beverage filling device for filling bottles with liquid beverage filling material. The filling devices may have an apparatus being configured to introduce a predetermined volume of liquid beverage filling material into the interior of bottles to a substantially predetermined level of liquid beverage filling material, and the apparatus configured to introduce a predetermined flow of liquid beverage filling material comprising apparatus being configured to terminate the filling of beverage bottles upon liquid beverage filling material reaching said substantially predetermined level in bottles. There may also be provided a conveyer arrangement being configured and disposed to move bottles, for example, from an inspecting machine to the filling machine.

Upon filling, a closing station closes filled bottles.

There may further be provided a conveyer arrangement configured to transfer filled bottles from the filling machine to the closing station, a labeling station in the event that labeling of the filled bottles is intended, as well as a loading station that is configured to load filled bottles into containers, for example, in a six-pack arrangement. There may also be provided a conveyor arrangement configured to transfer filled bottles from the closing station to the loading station, and to and from the labeling station.

Devices for cleaning containers, such as, for example, bottles, cans, boxes, and the like are used to clean and/or sterilize beverage containers, such as, for example, plastic bottles, either interiorly or, as desired, exteriorly with a stream of air that contains hydrogen peroxide vapor being employed. This air stream comprises an elevated temperature necessary to maintain hydrogen peroxide in the vaporized state. In the event that the air stream covers or contacts vessel walls that are cooler, hydrogen peroxide condenses as a fine film at the contact locations. Such film achieves a uniform sterilization of the surface, when compared with prior designs wherein fine droplets are directly sprayed onto the surfaces.

In devices of this type, the evaporation of hydrogen peroxide that is usually present in aqueous solution having a suitable concentration, and that, accordingly, is evaporated together with the water, is done in an evaporation chamber of a hydrogen peroxide evaporator, from which evaporator the hydrogen peroxide vapor, through which air has been blown, is passed to the container that is to be sterilized. In such arrangements, generally, one evaporator is provided for each container position, and one evaporator is cyclically utilized to sterilize containers that are introduced sequentially.

In known designs, as they are known from German Patent No. DE 32 35 476 C2, German Patent No. DE 35 40 161 C2, and German Patent No. DE 39 00 448 C2 (FIG. 2), hydrogen peroxide is sprayed, by means of a two-component nozzle, into the evaporator chamber. The spray droplets contact the heated surfaces and evaporate there. This method is superior to other methods in which evaporation is carried with heated air, since the heat capacity of air is much inferior to solids (wall material). German Patent No. DE 32 35 476 C2, and its corresponding U.S. Pat. No. 4,631,173 issued to Müller et al. on Dec. 23, 1986; German Patent No. DE 35 40 161 C2, and its corresponding U.S. Pat. No. 4,896,478 issued to Reiter on Jan. 30, 1990; and German Patent No. DE 39 00 448 C2, and its corresponding U.S. Pat. No. 4,987,721 issued to Turtschan on Jan. 29, 1991, are hereby incorporated by reference as if set forth in their entirety herein.

A similar design is known from German Patent No. DE 19 704 639 C2. Therein, a single-component nozzle is used to spray an airstream that has been admitted in a different manner, onto the wall surfaces in the evaporation chamber, which wall surfaces, due to specific reasons, are maintained at a temperature that is below the evaporation temperature. Evaporation is carried out at a higher wall temperature only in the further extent of the air stream. German Patent No. 19 704 639 C2 and its corresponding U.S. Pat. No. 6,339,678 issued to Sorensen on Jan. 15, 2002, are hereby incorporate by reference as if set forth in their entirety herein It is of disadvantage in this type of art that single-component or two-component nozzles are used, which, as is known, operate with very narrow channels that effectuate atomization. Atomization into very fine droplets, however, is necessary, so as to subsequently achieve a rapid evaporation.

In the known designs, the nozzles tend to become rapidly plugged. This is due to the stabilizing salts that are usually present in hydrogen peroxide/water solutions, and that tend to precipitate and tend to form small grains that cause the narrow nozzle channels to become plugged. This effect is only insufficiently prevented by filters that are disposed downstream of the flow.

OBJECTS

One object of an embodiment described below is to solve the problems encountered on similar apparatus of the prior art.

Another object or aim of the present application is to configure a device of the type discussed herein that is free of plugging.

SUMMARY

One feature or aspect of an embodiment is believed at the time of the filing of this patent application to possibly reside broadly in a bottling plant for filling bottles with liquid beverage filling material, said bottling plant comprising: a filling machine being configured and disposed to fill cleaned bottles with liquid beverage filling material; said filling machine comprising: a rotor being configured and disposed to rotate around a vertical machine axis and having a peripheral portion; a plurality of filling positions disposed at said peripheral portion of said rotor; each of said plurality of filling positions comprising: a bottle carrier being configured and disposed to provide bottles for filling; a filling device being disposed above a bottle carrier and configured to fill a bottle disposed on said bottler carrier; each filling device comprising: apparatus configured to introduce a predetermined volume of liquid beverage filling material into the interior of bottles to a predetermined level of liquid beverage filling material; apparatus configured to terminate the filling of bottles upon liquid beverage filling material reaching the predetermined level in bottles; a cleaning station being configured and disposed to clean bottles prior to filling with a liquid beverage filling material; apparatus configured and disposed to move bottles to said cleaning station; said cleaning apparatus comprising: a body comprising an interior, and exterior, an inlet structure, and an outlet structure; said interior comprising a chamber; said inlet structure comprising a first nozzle being configured and disposed in a first position to inject a jet of air in a first direction into and against a wall of said chamber; said inlet structure comprising a second nozzle being configured and disposed in a second position to inject a jet of cleaning medium in a second direction into said chamber; the first direction being transverse to the second direction; said first nozzle and said second nozzle being configured and disposed to direct a stream of air laden with cleaning medium droplets against a wall of said chamber; apparatus being configured and disposed to heat said chamber to a temperature sufficient to vaporize cleaning medium droplets deposited on the wall of said chamber; said outlet structure also being configured and disposed to permit delivery of a mixture of air and vaporized cleaning medium through said outlet structure of said body and into the interior of a bottle to be cleaned; and apparatus being configured and disposed to terminate delivery of a mixture of air and vaporized cleaning medium from said outlet structure; said bottling plant further comprising: a closing station being configured and disposed to close bottles filled with liquid beverage filling material; apparatus being configured and disposed to move bottles filled with liquid beverage filling material from said filling machine to said closing station; apparatus being configured and disposed to containerize bottles filled with liquid beverage filling material; apparatus being configured and disposed to move filled bottles from said closing station to said containerization station; and control apparatus being configured and disposed to control at least operation of said filling machine.

Another feature or aspect of an embodiment is believed at the time of the filing of this patent application to possibly reside broadly in a method of operating a cleaning station configured to clean containers in a container filling plant configured to fill beverage containers with a liquid beverage filling material, said container cleaning station comprising: a body comprising an inlet structure and an outlet structure; said inlet structure comprising a structure being configured and disposed to provide a flow of air in a first direction; said inlet structure comprising a structure being configured and disposed to provide a flow of cleaning medium in a second direction transverse to the flow of air to mix air and cleaning medium; a heating arrangement being configured and disposed to heat and vaporize cleaning medium in said body; and said outlet structure being configured and disposed to direct delivery of a mixture of air and vaporized cleaning medium onto at least one surface of a container to be cleaned; said method comprising the steps of: injecting a flow of air in a first direction into said body with said structure being configured and disposed to provide a flow of air in a first direction; impinging said flow of air with a flow of cleaning medium in a second direction with said structure being configured and disposed to provide a flow of cleaning medium in a second direction, which second direction being transverse to the flow of air to mix air and cleaning medium; vaporizing cleaning medium in said body; and directing a mixture of air and vaporized cleaning medium onto at least one surface of a container to be cleaned.

Another feature or aspect of an embodiment is believed at the time of the filing of this patent application to possibly reside broadly in a cleaning station for a container filling plant configured to fill beverage containers with a liquid beverage filling material, said cleaning station comprising: a body comprising an inlet structure and an outlet structure; said inlet structure comprising a structure being configured and disposed to provide a flow of air in a first direction; said inlet structure comprising a structure being configured and disposed to provide a flow of cleaning medium in a second direction transverse to the flow of air to mix air and cleaning medium; a heating arrangement being configured and disposed to heat and vaporize cleaning medium in said body; and said outlet structure being configured and disposed to direct delivery of a mixture of air and vaporized cleaning medium onto at least one surface of a container to be cleaned.

Another feature or aspect of an embodiment is believed at the time of the filing of this patent application to possibly reside broadly in a device for sterilizing or cleaning of containers, such as, beverage containers and the like by impinging them with a flow consisting of a mixture of air and hydrogen peroxide, comprising a hydrogen peroxide evaporator that has an evaporation chamber, with heated walls, through which chamber air flows, and against whose walls hydrogen peroxide is sprayed by means of a nozzle device, characterized in that the nozzle device comprises an air nozzle that is blowing a narrow air jet and a hydrogen peroxide nozzle that is adapted to generate a hydrogen peroxide jet at a distance from the air jet which hydrogen peroxide jet is directed onto the air jet.

In accordance with one aspect of the application, atomization is done using a jet arrangement in which a jet of air and a jet of hydrogen peroxide are generated separately from one another. They meet in a free space, whereby at the point of crossing, the air jet disrupts the hydrogen peroxide jet into small droplets. No atomization is done within the hydrogen peroxide nozzle, but instead a solid stream is generated. The required nozzle channels comprise cross-sections of such a size that they are not plugged by salt crystals.

The features that the evaporation chamber comprises an annular configuration and that the air nozzle is configured to produce a jet that is directed tangentially with respect to the evaporation chamber are of advantage. Thus, in such embodiment, the droplets are blown, together with the air jet, in circular manner through the chamber that comprises an annular configuration and are deposited by centrifugal force with a large surface area at the outer surface of the chamber that comprises an annular configuration, where they evaporate very rapidly.

The feature that the evaporation chamber is connected to the outlet of the evaporator by means of heated channels is of advantage. In this manner, upon evaporation in the evaporation chamber in the further, or downward-leading, channels, as required, further evaporation can be done in the event that droplets that have not been evaporated are present in the air jet. Furthermore, a stable temperature can be maintained at the desired temperature in the channels up to the outlet.

The above-discussed embodiments of the present invention will be described further hereinbelow. When the word "invention" or "embodiment of the invention" is used in this specification, the word "invention" or "embodiment of the invention" includes "inventions" or "embodiments of the invention", that is the plural of "invention" or "embodiment of the invention". By stating "invention" or "embodiment of the invention", the Applicant does not in any way admit that the present application does not include more than one patentably and non-obviously distinct invention, and maintains that this application may include more than one patentably and non-obviously distinct invention. The Applicant hereby asserts that the disclosure of this application may include more than one invention, and, in the event that there is more than one invention, that these inventions may be patentable and non-obvious one with respect to the other.

BRIEF DESCRIPTION OF THE DRAWINGS

The application is explained in greater detail below with reference to the accompanying drawings.

FIG. 1B illustrates the arrangement for cleaning containers in accordance with one embodiment of the present application;

DESCRIPTION OF EMBODIMENT OR EMBODIMENTS

Figure 1A:
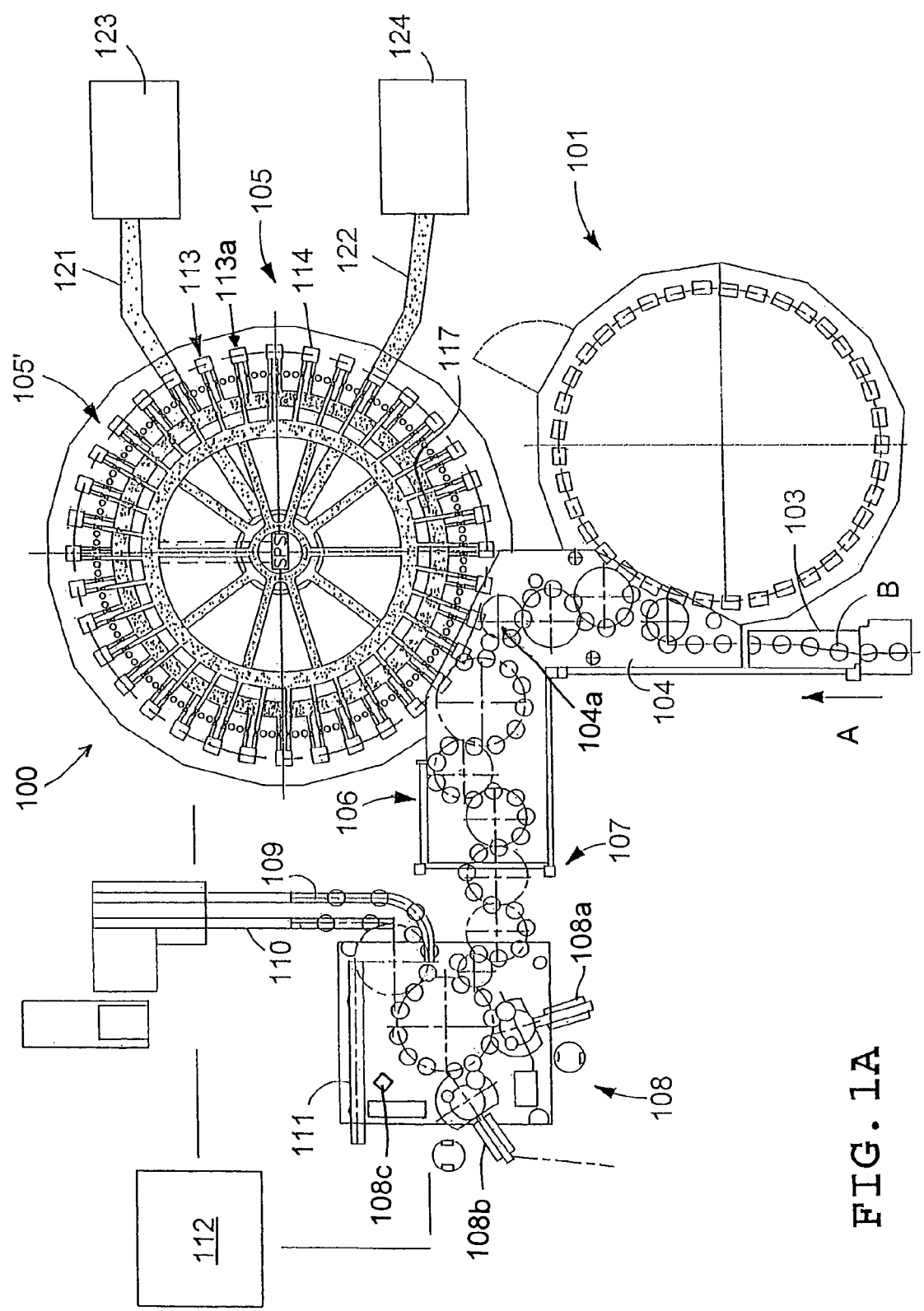
FIG. 1A is a schematic illustration of a container filling plant in accordance with one embodiment of the present application.

FIG. 1A shows schematically the main components of one embodiment example of a system for filling containers, specifically, an embodiment of a beverage bottling plant 100 for filling bottles B with liquid beverage filling material, in accordance with one embodiment, or in which system or plant could possibly be utilized at least one aspect, or several aspects, of the embodiments disclosed herein.

FIG. 1A shows a rinser or rinser station 101, to which the containers, namely bottles B, are fed in the direction of travel as is indicated by the arrow A, by means of a conveyer line or conveyer arrangement 103, and downstream of rinser station 101, in the direction of travel as is indicated by the arrow A, the rinsed bottles B are transported to a beverage filling machine 105 by means of a conveyer line or conveyer arrangement 104 that is formed, for example, by a star wheel conveyer or a plurality of star wheels of a conveyer arrangement. The conveyer arrangement 104 may possibly have a star wheel 104a that introduces bottles B to the filling machine 105.

Downstream of the filling machine 105, in the direction of travel of the bottles B, there can preferably be a closer or closer station 106 which closes the bottles B.

The closer or closer station 106 can, for example, be connected directly to a labeling device or labeling station 108, such as, for example, by means of a conveyer line or conveyer arrangement 107 that may be formed, for example, by a plurality of star wheels of a conveyer arrangement.

In the illustrated embodiment, the labeling device or labeling machine or labeling station 108 has, for example, three outputs, namely one output formed by a conveyer or conveyer arrangement 109 for bottles B that are filled with a first product. The first product may possibly be provided by a product mixer 123 that is connected to the filling machine 105, for example, through a conduit 121, and bottles B that are filled with a predetermined volume of liquid beverage filling material, that is, the first product, are then labeled by a labeling module 108a in the labeling stations 108 corresponding to this first product delivered from product mixer 123 to the beverage filling machine 105 and thence to the corresponding bottles B.

A second output that is formed by a conveyer or conveyer arrangement 110 is provided for those bottles B that are filled with a second product. The second product may emanate from a second product mixer 124 that is connected, for example, through a conduit 122 to the filling machine 105, and these bottles B filled with a predetermined volume of liquid beverage filling material comprising the second product are then correspondingly labeled by a labeling module 108b in the labeling station 108 corresponding to this second product.

A third output, for example, formed by a conveyer or conveyer arrangement 111, removes any bottles B which have been incorrectly labeled as may have been determined by an inspecting device or an inspecting station, or an inspecting module 108c that may possibly form a part of the labeling station 108.

In FIG. 1A item 112 is a central control unit or, expressed differently, a controller or a system which includes a process controller that, among other things, controls the operation of the above-referenced system or plant.

The beverage filling machine 105 is preferably of the revolving design, with a rotor 105', which revolves around a vertical machine axis. On the periphery of the rotor 105' there are a number of filling positions 113, each of which comprises bottle carriers or container carriers 113a that are configured and disposed to present bottles B for filling, as well as a filling device or element or apparatus 114 located or configured to be located above the corresponding container carrier 113a and the corresponding bottle B presented by the carrier 113a. The filling device or apparatus 114 comprises an apparatus configured to introduce a predetermined volume of liquid beverage filling material into the interior of bottles B to a predetermined level of liquid beverage filling material. Furthermore, the filling device or apparatus comprises an apparatus configured to terminate the filling of bottles upon liquid beverage filling material reaching the predetermined level in bottles B. In other words, filling elements 114 are configured and disposed to provide a predetermined flow of liquid beverage filling material from the source thereof, such as, product mixers 123 and 124, into the bottles B.

The toroidal vessel 117 is a component, for example, of the revolving rotor 105'. The toroidal vessel 117 can be connected by means of a rotary coupling or a coupling that permits rotation, and by means of an external connecting line 121 to the external reservoir or product mixer 123 to supply the product, that is, product mix one, for example.

As well as the more typical filling machines having one toroidal vessel, it is possible that in at least one possible embodiment a filling machine could possibly be utilized wherein each filling device 114 is preferably connected by means of two connections to a toroidal vessel 117 which contains a first product, say by means of a first connection, for example, 121, and to a second toroidal vessel which contains a second product, say by means of the second connection, for example, 122. In this case, each filling device 114 can also preferably have, at the connections, two individually-controllable fluid or control valves, so that in each bottle B which is delivered at the inlet of the filling machine 105 to a filling position 113, the first product or the second product can be filled by means of an appropriate control of the filling product or fluid valves.

It will be understood that while a two-product assembly or system of a bottling plant is illustrated in FIG. 1A, the disclosure is equally applicable to single-product installations, or other commensurate embodiments.

With reference to FIG. 1B, there is illustrated in a schematic representation an arrangement or system which may be part of a container filling plant as described in the foregoing, the other parts of which are not illustrated. Also illustrated are containers that may possibly be manufactured from thermoplastic-coated cardboard blanks. In operation of the system, the containers are sterilized, filled with a product, such as milk, for example, and finally sealed. Filling plants and filling plant systems of this type are known and need not be specified in greater detail herein.

Packages or containers 12 are transported on a schematically illustrated conveyor 14, which may be a cell chain or similar mechanism, in which they are held positively and, for example, in upright position. The conveyor 14 advances packages 12 at regular intervals in the direction indicated by the arrow E. At the conveyor entrance 15 the packages 12 pass through a sterilization or cleaning station 16 and then through a dryer station 18 that possibly consists of five individual positions, each operating with its own work interval.

A combination atomizer, evaporator, and spray device 20, which will be described in greater detail below, is mounted above the path of packages 12 in the sterilization station 16, which is labeled on the whole with reference number 16.

The device 20 has an outlet structure 1 that is configured and disposed to direct a stream 2 comprising air and a cleaning agent vapor onto and/or into containers 12. The device 20 has a body 3 that is heated by heaters 25 that are shown schematically only but serve to heat the body 3 sufficiently to vaporize the cleaning medium. The device or arrangement 20 communicates through a line or conduit 22 with a reservoir (not shown) of liquid cleaning agent, which may, for example, be a 35% aqueous solution of hydrogen peroxide. Line 22 may possibly contain a known metering device, through which precisely measured portions of cleaning agent are supplied to the device 20. Device 20 also communicates through a line 24 with a source of compressed air (not shown), such as a compressor, for example, as known in the art. The supply of compressed air is monitored and controlled by controls (not shown) as known in the art. The positions of lines 22 and 24 are shown schematically only in FIG. 1B and the actual positioning of the outputs of the lines 22 and 24 is explained in greater detail below.

Heated sterile air is supplied through a line 26 to a hot-air distributor 28 in the dryer station 18. Blower nozzles 30 are positioned extending down from hot-air distributor 28 in such a way that they can blow a specific amount of sterile hot air at a specific temperature (80 degrees Celsius, for example) into the packages 12 in each of the five individual positions in dryer station 18. This air is obtained from an air reservoir (not shown) and heated in a heater (not shown) as known in the art.

There is also possibly provided a reaction station 32 that the packages 12 travel through, for example, in two work intervals, upstream of the dryer station 18. The cleaning agent and air mixture that is injected through outlet structure 1 into and onto the containers 12 is allowed to remain on the corresponding surfaces of the containers 12 as they travel through the reaction station 32 so that the air and cleaning agent mixture will have sufficient time to completely kill off even especially resistant germs.

While generally a linear direction of travel has been indicated in FIG. 1B, it will be appreciated that the system is applicable to other types of direction of travel.

In at least one possible embodiment the body 3 comprises a first portion 3a and a second portion 3b that are secured to one another as is schematically indicated by a fastener system 33. Furthermore, the flow of cleaning medium 2 may be terminated at outlet 1 by apparatus 34 configured to terminate the flow of cleaning medium at outlet 1.

Figure 1:
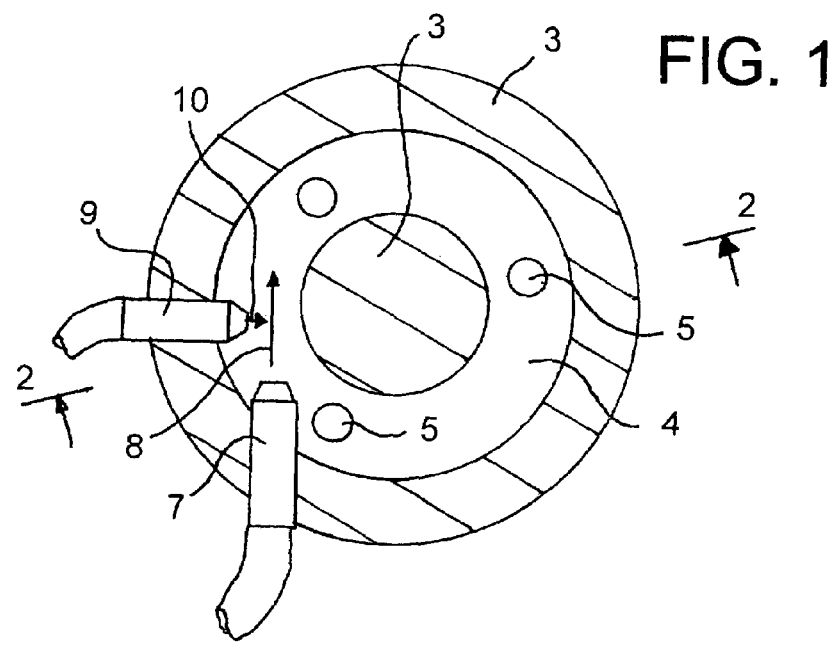
FIG. 1 is a cross-section along line 1—1 in FIG. 2 through a hydrogen peroxide evaporator in accordance with one embodiment of the present application.
Figure 2:
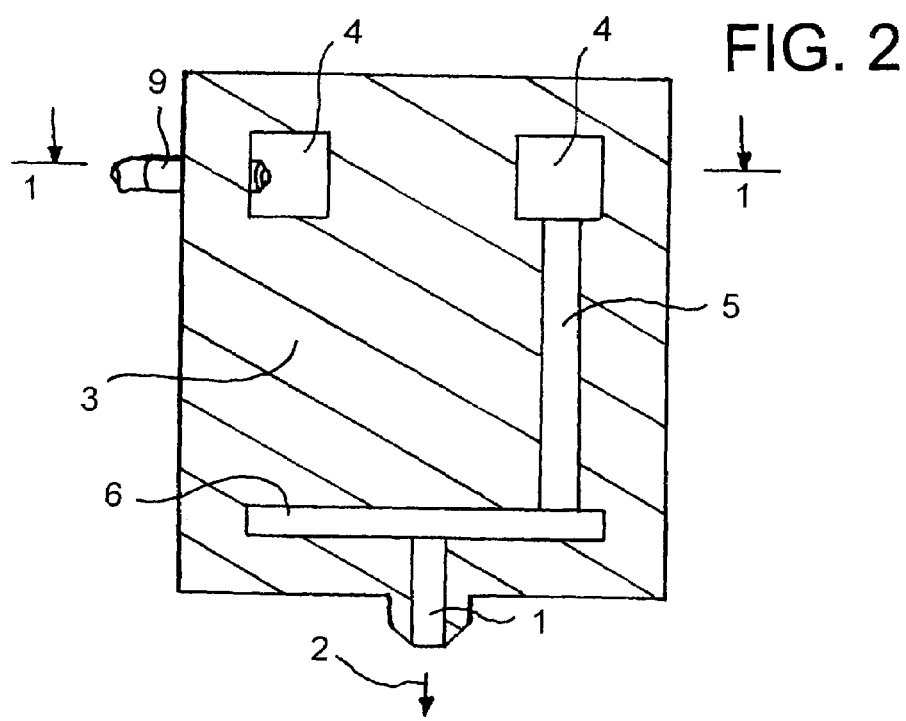
FIG. 2 is a cross-section along line 2—2 in FIG. 1.

With respect to the device 20 of FIG. 1B, that comprises a hydrogen peroxide evaporator illustrated in FIGS. 1 and 2, this is a part of a device for cleaning and/or sterilizing beverage containers, such as bottles B and containers 12. At its outlet 1, the evaporator generates a stream 2 comprising air and a portion of hydrogen peroxide vapor, as well as water vapor, as present, in the event that hydrogen peroxide in the usual aqueous solution having suitable concentration is used. The outlet 1 can be disposed, as is known, for example, above the inlet of a bottle or another beverage container, so as to sterilize the interior.

The illustrated evaporator comprises a massive housing block 3, that can be separated and connected at separating surface that are not shown, and an annular channel 4 is formed in the portion of the housing block that is opposite of the outlet 1. In the embodiment example, the annular channel 4 is connected to the outlet 1 by way of three channels 5 that extend parallel to the axis of the outlet 1, and all three channels 5 lead into a collection chamber 6.

The housing block or body 3 comprises heating devices (not shown) that heat the housing block to a temperature that is suitable for evaporating the hydrogen peroxide, such that all its inner walls also attain a corresponding temperature.

As is shown in FIG. 1, an air nozzle 7 leads in tangential manner into the annular channel 4, the air nozzle generates a bundled air jet 8, that is introduced in tangential manner, and the air nozzle generates a circular flow in the annular channel 4, while the air stream flows from the annular chamber to the outlet 1 via the channels 5 and the collection chamber 6.

A hydrogen peroxide nozzle 9 is disposed in the housing block 3 in such a way that it generates a liquid jet 10 transverse to the air jet 8 at a distance from the air jet, and this is done in such a way that the liquid jet 10 impinges on the air jet 8 in free space within the annular channel 4.

The hydrogen peroxide nozzle 9 is configured in such a manner that it generates a solid stream, liquid jet that has a diameter of a few tenths of a millimeter. Salt crystals present in the hydrogen peroxide or, respectively, in the mixture comprising hydrogen peroxide/water that is usually used, or other solids that lead to plugging when use is made of customary nozzles, are permitted to pass through nozzle as a liquid jet of this thickness without difficulties and without the hydrogen peroxide nozzle 9 becoming plugged.

The liquid jet 10 impinges on the air jet 8 at a point of crossing and is taken along by this air jet by means of streaming air that is flowing with a suitable stream velocity, and the liquid jet is shredded into droplets. In at least one possibly embodiment of the application this interaction of the stream of air and the stream laden with hydrogen peroxide may possibly entail atomization of the hydrogen peroxide droplets. The spray mist comprising fine droplets that is generated in this manner, moves, together with the air jet, that is generated by the air jet 8 that is introduced in tangential manner, in a circular manner in the annular channel. Hereby, the fine liquid droplets generated at the point of crossing of the jets are transported, by centrifugal force, substantially completely, to the circumferential wall of the annular chamber 4, so as to be deposited thereon.

There the droplets evaporate. The mixture of air and hydrogen peroxide-water vapor subsequently also passes through the channels 5, that are also heated, to the outlet 1. As required, any liquid droplets still present can be subjected to post-evaporation in the channels 5, and a re-condensation in the evaporator is precluded.

In an embodiment that is not illustrated, instead of the annular chamber 4, any other evaporation chamber may be provided in which the spraying of hydrogen peroxide by crossing jets of air and liquid is carried out. It is preferred that such a chamber can have a round circumferential wall and the air jet 8 is tangentially blown in, as is illustrated in FIG. 1, so as to generate similar effects as in the case of an annular chamber.

Instead of straight channels 5, also circuitous paths, for example, spirally disposed channels, can be provided between the evaporator chamber 4 and the outlet 1, so as to effectuate an improved post-heating over a longer distance.

It will be appreciated that the application is applicable to new containers and correspondingly to recycled containers. The containers may be of any variety and including, but not limited to, bottles, glass bottles or plastic bottles, cardboard containers, plastic containers, cans, cup-shaped containers, and the like receptacles.

In at least one possible embodiment of the present application the stream of air may be injected into a stream of cleaning medium, for example, a stream containing hydrogen peroxide, so as to atomize the cleaning medium, for example, hydrogen peroxide.

One feature or aspect of an embodiment is believed at the time of the filing of this patent application to possibly reside broadly in a device for sterilizing of beverage containers by impinging them with a flow consisting of a mixture of air and hydrogen peroxide, comprising a hydrogen peroxide evaporator that has an evaporation chamber 4, with heated walls, through which chamber air flows, and against whose walls hydrogen peroxide is sprayed by means of a nozzle device 7, 9, characterized in that the nozzle device comprises an air nozzle 7 that is blowing a narrow air jet 8 and a hydrogen peroxide nozzle 9 that is adapted to generate a hydrogen peroxide jet 10 at a distance from the air jet which hydrogen peroxide jet is directed onto the air jet.

Another feature or aspect of an embodiment is believed at the time of the filing of this patent application to possibly reside broadly in the device characterized in that the evaporation chamber 4 comprises an annular configuration and the air nozzle 7 is configured to produce a jet that is directed tangentially with respect to the evaporation chamber.

Yet another feature or aspect of an embodiment is believed at the time of the filing of this patent application to possibly reside broadly in the device characterized in that the evaporation chamber is connected to the outlet of the evaporator by means of heated channels.

Some examples of bottling systems that may possibly be utilized or possibly adapted for use in at least one possible embodiment of the present application may possibly be found in the following U.S. patents, all assigned to the Assignee herein, namely: U.S. Pat. No. 4,911,285; No. 4,944,830; No. 4,950,350; No. 4,976,803; No. 4,981,547; No. 5,004,518; No. 5,017,261; No. 5,062,917; No. 5,062,918; No. 5,075,123; No. 5,078,826; No. 5,087,317; No. 5,110,402; No. 5,129,984; No. 5,167,755; No. 5,174,851; No. 5,185,053; No. 5,217,538; No. 5,227,005; No. 5,413,153; No. 5,558,138; No. 5,634,500; No. 5,713,403; No. 6,276,113; No. 6,213,169; No. 6,189,578; No. 6,192,946; No. 6,374,575; No. 6,365,054; No. 6,619,016; No. 6,474,368; No. 6,494,238; No. 6,470,922; No. 6,463,964; No. 6,470,922; No. 6,474,368; No. 6,484,477; No. 6,494,238; and No. 6,619,016.

The components disclosed in the various publications, disclosed or incorporated by reference herein, may possibly be used in possible embodiments of the present invention, as well as equivalents thereof.

All of the patents, patent applications or patent publications, which were cited in the International Search Report of the European Patent Office, dated Nov. 11, 2002, and/or cited elsewhere are hereby incorporated by reference as if set forth in their entirety herein as follows: U.S. Pat. No. 4,797,255 issued to Hatanaka et al. on Jan. 10, 1989; European Patent No. EP 0 312 908, corresponding to U.S. Pat. No. 5,078,976 issued to Shibauchi et al. on Jan. 7, 1992; U.S. Pat. No. 5,152,968 issued to Foti et al. on Oct. 6, 1992; International Patent No. WO 99 30747, corresponding to U.S. Pat. No. 6,596,231 issued to Catelli et al. on Jul. 22, 2003; and U.S. Pat. No. 5,873,181 issued to Miyasaki on Feb. 23, 1999 and its related U.S. Pat. No. 5,711,819 issued to Miyasaki on Jan. 27, 1998.

Some examples of apparatus and methods of sterilizing or cleaning containers that may possibly be utilized or possibly adapted for use in at least one possible embodiment of the present application may possibly be found in the following U.S. patents: U.S. Pat. No. 5,092,356 issued to Grot on Mar. 3, 1992; U.S. Pat. No. 5,320,144 issued to Ahlers on Jun. 14, 1994; U.S. Pat. No. 5,533,552 issued to Ahlers on Jul. 9, 1996; U.S. Pat. No. 5,558,135 issued to Kronseder et al. on Sep. 24, 1996; and U.S. Pat. No. 5,896,899 issued to Schlitz on Apr. 27, 1999.

The corresponding foreign and international patent publication applications, namely, Federal Republic of Germany Patent Application No. 101 45 818.5, filed on Sep. 17, 2001, having inventors Holger GROSSMANN and Dr. Thomas HEROLD, and German Laid Open Patent Application No. DE-OS 101 45 818, having inventors Holger GROSSMANN and Dr. Thomas HEROLD, and German Patent No. DE-PS 101 45 818, having inventors Holger GROSSMANN and Dr. Thomas HEROLD, and International Patent Application No. PCT/EP02/08860, filed on Aug. 8, 2002, having WIPO Publication No. WO03/024492, and having inventors Holger GROSSMANN and Dr. Thomas HEROLD, as well as their published equivalents, and other equivalents or corresponding applications, if any, in corresponding cases in the Federal Republic of Germany and elsewhere, and the references and documents cited in any of the documents cited herein, such as the patents, patent applications and publications, are hereby incorporated by reference as if set forth in their entirety herein.

Some examples of sterilizing or cleaning agents and concentrations thereof that may possibly be utilized or possibly adapted for use in at least one possible embodiment of the present application may possibly be found in the following U.S. patents: U.S. Pat. No. 6,039,922 issued to Swank et al. on Mar. 21, 2000; U.S. Pat. No. 6,244,275 issued to Ziegler et al. on Jun. 12, 2001; U.S. Pat. No. 6,406,666 issued to Cicla et al. on Jun. 18, 2002; and U.S. Pat. No. 6,612,149 issued to Wang et al. on Sep. 2, 2003.

The appended drawings in their entirety, including all dimensions, proportions and/or shapes in at least one embodiment of the invention, are accurate and are hereby included by reference into this specification.

Some examples of nozzle structures that may possibly be utilized or possibly adapted for use in at least one possible embodiment of the present application may possibly be found in the following U.S. patents: U.S. Pat. No. 6,042,026 issued to Buehler, II on Mar. 28, 2000; U.S. Pat. No. 6,394,366 issued to Adams on May 28, 2002; U.S. Pat. No. 6,402,062 issued to Bendig et al. on Jun. 11, 2002; U.S. Pat. No. 6,616,072 issued to Harata et al. on Sep. 9, 2003; U.S. Pat. No. 6,666,386 issued to Huang on Dec. 23, 2003; and U.S. Pat. No. 6,681,498 issued to Steffan on Jan. 27, 2004.

All, or substantially all, of the components and methods of the various embodiments may be used with at least one embodiment or all of the embodiments, if more than one embodiment is described herein.

Some examples of heater arrangement that may possibly be utilized or possibly adapted for use in at least one possible embodiment of the present application may possibly be found in the following U.S. patents: U.S. Pat. No. 6,404,421 issued to Meijler et al. on Jun. 11, 2002; U.S. Pat. No. 6,515,264 issued to Toya et al. on Feb. 4, 2003; U.S. Pat. No. 6,548,786 issued to Takizawa et al. on Apr. 15, 2003; U.S. Pat. No. 6,555,796 issued to Cusack on Apr. 29, 2003; U.S. Pat. No. 6,633,727 issued to Henrie et al. on Oct. 14, 2003; and U.S. Pat. No. 6,677,557 issued to Ito et al. on Jan. 13, 2004.

All of the references and documents, cited in any of the documents cited herein, are hereby incorporated by reference as if set forth in their entirety herein. All of the documents cited herein, referred to in the immediately preceding sentence, include all of the patents, patent applications and publications cited anywhere in the present application.

Some examples of induction heating systems and methods that may possibly be utilized or possibly adapted for use in at least one possible embodiment of the present application may possibly be found in the following U.S. patents: U.S. Pat. No. 6,011,246 issued to Bonzano et al. on Jan. 4, 2000; U.S. Pat. No. 6,148,019 issued to Fishman et al. on Nov. 14, 2000; U.S. Pat. No. 6,211,498 issued to Partridge et al. on Apr. 3, 2001; U.S. Pat. No. 6,323,469 issued to Bissdorf et al. on Nov. 27, 2001; U.S. Pat. No. 6,456,818 issued to Nakayama et al. on Sep. 24, 2002; and U.S. Pat. No. 6,608,291 issued to Collins et al. on Aug. 19, 2003.

Some examples of microwave heating systems and methods that may possibly be utilized or possibly adapted for use in at least one possible embodiment of the present application may possibly be found in the following U.S. patents: U.S. Pat. No. 4,938,673 issued to Adrian on Jul. 3, 1990; U.S. Pat. No. 4,963,709 issued to Kimrey, Jr. on Oct. 16, 1990; U.S. Pat. No. 5,202,541 issued to Patterson et al. on Apr. 13, 1993; U.S. Pat. No. 5,220,142 issued to LaMaire et al. on Jun. 15, 1993; U.S. Pat. No. 6,093,921 issued to Gaisford et al. on Jul. 25, 2000; and U.S. Pat. No. 6,674,056 issued to Lee on Jan. 6, 2004.

It will be understood that the examples of patents, published patent applications, and other documents which are included in this application and which are referred to in paragraphs which state "Some examples of . . . which may possibly be used in at least one possible embodiment of the present application . . . " may possibly not be used or useable in any one or more embodiments of the application.

The sentence immediately above relates to patents, published patent applications and other documents either incorporated by reference or not incorporated by reference.

Thus, one feature or aspect of an embodiment is believed at the time of the filing of this patent application to possibly reside broadly in a device for sterilizing of beverage containers by impinging them with a flow consisting of a mixture of air and hydrogen peroxide, comprising a hydrogen peroxide evaporator that has an evaporation chamber (4), with heated walls, through which chamber air flows, and against whose walls hydrogen peroxide is sprayed by means of a nozzle device (7, 9), is characterized in that the nozzle device comprises an air nozzle (7) that is blowing a narrow air jet (8), and comprises a hydrogen peroxide nozzle (9) that is adapted to generate a hydrogen peroxide jet (10) at a distance from the air jet and which hydrogen peroxide jet is directed onto the air jet.

The embodiments of the invention described herein above in the context of the preferred embodiments are not to be taken as limiting the embodiments of the invention to all of the provided details thereof, since modifications and variations thereof may be made without departing from the spirit and scope of the embodiments of the invention.

What is claimed is:

1. A bottling plant for filling bottles with liquid beverage filling material, said bottling plant comprising:
    a bottle filling machine being configured and disposed to fill bottles with liquid beverage filling material;
    said filling machine comprising:
        a rotor being configured and disposed to rotate around a vertical machine axis and having a peripheral portion;
        a plurality of filling positions disposed at said peripheral portion of said rotor; and
        each of said plurality of filling positions comprising:

a bottle carrier being configured and disposed to provide bottles for filling; and a filling device being disposed above said bottle carrier and configured to fill a bottle disposed on said bottler carrier to a predetermined level of liquid beverage filling material;

a bottle closing machine being configured and disposed to close filled bottles;

a first conveyor arrangement being configured and disposed to move filled bottles from said filling machine to said closing machine;

a bottle packing machine being configured and disposed to pack closed, filled bottles;

a second conveyor arrangement being configured and disposed to move closed, filled bottles from said closing machine to said packaging machine; and a cleaning machine being configured and disposed to clean bottles prior to filling with a liquid beverage filling material;

a third conveyor arrangement being configured and disposed to move bottles to said cleaning station from a supply of bottles;

a fourth conveyor arrangement being configured and disposed to move cleaned bottles from said cleaning station to said filling machine; and said cleaning machine comprising:

a body comprising an inner vaporization chamber, an inlet structure, and an outlet structure;

said chamber having chamber walls;

a heating arrangement being configured and disposed to heat said chamber walls to a temperature sufficient to vaporize cleaning medium droplets deposited on said chamber walls;

said inlet structure comprising a first nozzle being configured and disposed in a first position to inject a jet of air in a first direction into said chamber;

said inlet structure comprising a second nozzle being configured and disposed in a second position to inject a jet of cleaning medium in a second direction into said chamber transverse to the first direction to impinge upon the jet of air to generate air laden with droplets of cleaning medium;

said first nozzle and said second nozzle being configured and disposed to direct the air laden with cleaning medium droplets against said heated chamber walls to vaporize the cleaning medium droplets to form a mixture of air and vaporized cleaning medium; and said outlet structure being configured and disposed to permit and control the flow of the mixture of air and vaporized cleaning medium from said chamber and into a bottle to be cleaned.

2. The bottling plant according to claim 1, wherein:
said chamber has a width dimension; and
said jet of air is substantially narrower than the width dimension of said chamber.

3. The bottling plant according to claim 2, wherein:
said vaporization chamber comprises an annular chamber having two circular concentric walls;
said air nozzle is positioned to direct a jet of air tangential to a concentric circular path disposed between said two circular annular concentric walls.

4. The bottling plant according to claim 3, wherein said body of said cleaning machine comprises a plurality of passages configured and disposed to connect said annular vaporization chamber and said outlet structure with one another.

5. The bottling plant according to claim 4, wherein said heating arrangement is configured and disposed to heat said body of said cleaning machine to thus heat said plurality of passages to maintain a mixture of air and cleaning medium within said plurality of passages at at least a temperature at which the cleaning medium is vaporized.

6. The bottling plant according to claim 5, wherein said plurality of passages connecting said annular vaporization chamber and said outlet structure comprises a collecting chamber configured and disposed to store a mixture of air and vaporized cleaning medium.

7. The bottling plant according to claim 6, wherein said plurality of passages comprises a plurality of vertical channels configured and disposed to connect said annular vaporization chamber and said collecting chamber with one another.

8. The bottling plant according to claim 7, wherein said plurality of passages comprise at least one of: straight passages and circuitous passages.

9. The bottling plant according to claim 8, wherein said body comprises:
at least a first portion and a second portion; and
fasteners to connect said first portion and said second portion to one another.

10. The bottling plant according to claim 9, wherein said outlet structure comprises a structure configured and disposed to inject a mixture of air and cleaning medium into the interior of a bottle to be cleaned.

11. The bottling plant according to claim 10, wherein said collecting chamber comprises an annular chamber having two circular annular concentric walls.

12. The bottling plant according to claim 1, wherein said cleaning medium comprises hydrogen peroxide in an aqueous solution.

13. The bottling plant according to claim 12, wherein:
said chamber has a width dimension; and
said jet of air is substantially narrower than the width dimension of said chamber.

14. The bottling plant according to claim 13, wherein:
said vaporization chamber comprises an annular chamber having two circular concentric walls;
said air nozzle is positioned to direct a jet of air tangential to a concentric circular path disposed between said two circular annular concentric walls.

15. The bottling plant according to claim 14, wherein said body of said cleaning machine comprises a plurality of passages configured and disposed to connect said annular vaporization chamber and said outlet structure with one another.

16. The bottling plant according to claim 15, wherein said heating arrangement is configured and disposed to heat said body of said cleaning machine to thus heat said plurality of passages to maintain a mixture of air and hydrogen peroxide within said plurality of passages at at least a temperature at which the hydrogen peroxide is vaporized.

17. The bottling plant according to claim 16, wherein said plurality of passages connecting said annular vaporization chamber and said outlet structure comprises a collecting chamber configured and disposed to store a mixture of air and vaporized hydrogen peroxide.

18. The bottling plant according to claim 17, wherein said plurality of passages comprises a plurality of vertical channels configured and disposed to connect said annular vaporization chamber and said collecting chamber with one another.

19. The bottling plant according to claim 18, wherein:
said plurality of passages comprise at least one of: straight passages and circuitous passages; and
said body comprises:
   at least a first portion and a second portion; and
   fasteners to connect said first portion and said second portion to one another.

20. The bottling plant according to claim 19, wherein:
said outlet structure comprises a structure configured and disposed to inject a mixture of air and hydrogen peroxide into the interior of a bottle to be cleaned; and
said collecting chamber comprises an annular chamber having two circular annular concentric walls.

* * * * *